United States Patent [19]

Maier

[11] 4,233,056
[45] Nov. 11, 1980

[54] NOVEL GLYCYLMETHYLPHOSPHINIC ACID DERIVATIVES, PROCESS FOR THEIR PRODUCTION AND USE THEREOF

[75] Inventor: Ludwig Maier, Arlesheim, Switzerland

[73] Assignee: Ciba-Geigy Corporation, Ardsley, N.Y.

[21] Appl. No.: 931,343

[22] Filed: Aug. 7, 1978

[30] Foreign Application Priority Data

Aug. 11, 1977 [CH] Switzerland ............... 9883/77

[51] Int. Cl.³ ............... A01N 57/10; C07F 9/30; C07F 9/32
[52] U.S. Cl. ............... 71/86; 71/71; 71/76; 71/78; 260/941; 260/502.5; 260/970
[58] Field of Search ............... 71/86, 71, 76, 78; 260/941, 502.5

[56] References Cited

U.S. PATENT DOCUMENTS

| | | | |
|---|---|---|---|
| 3,160,632 | 12/1964 | Toy et al. | 71/87 |
| 3,894,861 | 7/1975 | Hartman | 71/76 |
| 3,988,142 | 10/1976 | Franz | 71/86 |

OTHER PUBLICATIONS

Maier, Helv. Chim. Acta., vol. 50 (1967), 1742–1746.
Il'ina et al., Izv. Akad. Nuk. USSR., vol. 8 (1968), 1860–1862.
Ivanov et al., J. Gen. Chem., USSR, vol. 37 (1966), 1768–1773.

*Primary Examiner*—Catherine L. Mills
*Attorney, Agent, or Firm*—Harry Falber

[57] ABSTRACT

The present invention relates to novel herbicidally active and plant growth-regulating glycylmethylphosphinic acid derivatives of the formula

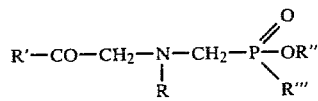

wherein R represents hydrogen, —CH₂COOH or an easily removable radical (e.g. benzyl, tert-butyl), R' represents a —OH or —OR₁ group, in which R₁ is a cation, a lower aliphatic radical, cycloalkyl or NH₂, R" represents hydrogen, a cation or lower alkyl and R''' represents optionally substituted alkyl or phenyl. These compounds are obtained by reacting a N-substituted glycine HOOC—CH₂—NH—R with formaldehyde and a phosphonous acid

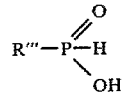

in a strongly acid solution and optionally removing the radical R by catalytic hydrogenation or with HBr. The compounds of the formula I are used as active ingredients of compositions especially for the post-emergent control of weeds or for inhibiting plant growth.

6 Claims, No Drawings

NOVEL GLYCYLMETHYLPHOSPHINIC ACID DERIVATIVES, PROCESS FOR THEIR PRODUCTION AND USE THEREOF

The present invention relates to novel glycylmethylphosphinic acid derivatives, processes for the production thereof and the use of these novel derivatives as active ingredients of herbicidal and plant growth-regulating compositions.

The novel glycylmethylphosphinic acid derivatives have the general formula I

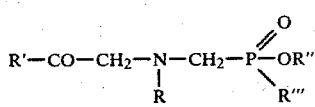

wherein

R represents hydrogen, a $C_1$–$C_6$alkyl radical, the group HOOC—$CH_2$—, and benzyl, diphenylmethyl or triphenylmethyl, R' represents a —OH or —$OR_1$ group, in which $R_1$ represents a cation, a substituted or unsubstituted $C_1$–$C_6$alkyl radical, a lower alkenyl or alkynyl radical, a cycloalkyl radical, or R' represents the amino group.

R" represents hydrogen, a cation, lower alkyl or hydroxyalkyl,

R'" represents a $C_1$–$C_4$alkyl radical which can be mono- or polysubstituted by hydroxyl, halogen or carboxyl, or represents a substituted or unsubstituted phenyl radical.

Preferably R is hydrogen or an easily removable radical (benzyl, tert-butyl, diphenylmethyl or triphenylmethyl).

If R' is the —OH group and/or R" is hydrogen, i.e. if the compounds of the formula I possess at least one free acid group, then such acids are able to form salts with bases, namely both with the carboxylic acid and the phosphinic acid group. Possible salts are the ammonium and metal salts of alkali metals and alkaline earth metals (Li, Na, K, Ca, Mg), and also of other metals, such as Fe, and salts of amines, such as alkylamines and alkenylamines, or of quaternary ammonio bases. Examples of amines are: methylamine, isopropylamine, tert-butylamine, allylamine.

If $R_1$ is a cycloalkyl radical, a lower alkenyl or alkynyl radical, or a substituted or unsubstituted alkyl radical, the end products are esters. Possible substituents of alkyl radicals $R_1$ are: halogen atoms, hydroxyl and lower alkoxy groups, and also carboxyl and cyano groups.

R" is lower alkyl, but is preferably hydrogen or a cation of the kind described in the definition of R'. A hydroxyalkyl radical R" is for example β-hydroxyethyl.

R'" is preferably a $C_1$–$C_4$alkyl radical, in particular methyl or ethyl. Examples of substituted alkyl radicals are hydroxymethyl, trichloromethyl, dichloromethyl, trifluoromethyl etc. Possible substituents of a substituted phenyl radical R'" are in particular halogen atoms, lower alkyl and haloalkyl groups as well as dialkylamino groups.

It is known that hypophosphorous acid with formaldehyde and piperidine (unsubstituted secondary amine) in a strong hydrochloric acid solution affords the hydrochloride of bis(piperidinomethyl)phosphinic acid [Helv. Chim. Acta 50, 1742 (1967)].

Successful attempts have also recently been made to react formaldehyde and hypophosphorous acid with functionally substituted secondary amines, such as N-substituted glycines, to give bis(glycylmethyl)phosphinic acids.

It has now been found that a similar reaction with corresponding alkyl- and arylphosphonous acids gives glycylmethylalkyl- or -arylphosphinic acids.

The process of the present invention for the production of the novel glycylmethylphosphinic acid derivatives of the formula I comprises reacting a N-substituted glycine of the formula II

wherein $R_2$ represents a $C_1$–$C_6$alkyl radical, preferably a removable alkyl radical such as the tert-butyl, benzyl, diphenylmethyl or triphenylmethyl radical or the group —$CH_2COOH$, with formaldehyde and a phosphonous acid of the formula III

wherein R'" is as defined in formula I, in an aqueous acid medium, and converting the resulting glycylmethylphosphinic acid derivative of the formula Ia

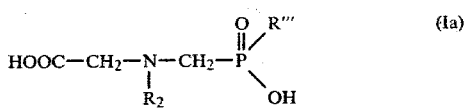

optionally by removing a removable group $R_2$ and/or further subsequent operations, into a salt or another derivative of the formula I.

In the starting glycine of the formula II, $R_2$ is preferably a removable radical, such as tert-butyl, benzyl, diphenylmethyl or triphenylmethyl, or else a further acetic acid group —$CH_2COOH$.

Instead of using the phosphonous acid of the formula III as such in the reaction mixture, it is also possible to use a corresponding dihalophosphine, especially a dichlorophosphine, of the formula R'"—$PCl_2$, which in the aqueous acid reaction medium is immediately hydrolysed to the phosphonous acid derivative of the formula III.

The reaction is advantageously carried out in a strong hydrochloric acid medium (pH < 5), in the temperature range between 20° and 100° C., and the reaction time is from about 2 to 4 hours. To prevent oxidation of the phosphonous acids the reaction is advantageously carried out with the exclusion of oxygen. Good yields are obtained especially by using an excess of formaldehyde.

If R'" is an alkyl radical in the starting material of the formula III and in the end product of the formula Ia, then this latter is obtained in the form of the hydrochloride. If, on the other hand, R'" is an electronegative substituent, such as hydroxymethyl, trichloromethyl or phenyl, the end products of the formula Ia crystallise without HCl, i.e. the phosphinic acid proton is so acidic that the resulting acids form an inner betaine.

If a starting material of the formula II is chosen in which $R_2$ is a removable group, $R_2$ can be removed after the reaction to give the phosphinic acid derivative of the formula Ia.

Eligible removable groups $R_2$ are tertiary $C_4$–$C_6$alkyl radicals, in particular tert-butyl, or aromatically substituted methyl groups, especially benzyl, and also diphenylmethyl and triphenylmethyl.

The removal of a phenylated methyl group, especially benzyl, is most appropriately effected by catalytic hydrogenation (catalytic debenzylation) with hydrogen in a solvent, such as water, glacial acetic acid, aqueous acetic acid or a mixture of water and ethanol.

A suitable catalyst is 5% palladium on carbon; but platinum oxide or platinum on carbon can also be used. The hydrogenation is preferably carried out under normal pressure and in the temperature range between 20° and 50° C. and, depending on the nature of the removable radical $R_2$, the reaction time is from 10 minutes to 20 hours.

A further possibility of removing this removable radical $R_2$ including a tertiary alkyl radical, such as in particular tert-butyl, consists in treating an acid of the formula Ia or a salt thereof (e.g. the hydrochloride) at 100°–200° C. with HBr in water or glacial acetic acid, optionally under pressure, for 1 to 10 hours.

The resulting derivatives of the formula I, in which R is hydrogen, are water-soluble and temperature stable both in the form of acids and salts. The conversion of acids of the formula I into corresponding salts, esters or amides, is effected by methods which are known in the art for carrying out such reactions, such as neutralisation, treatment of alcoholic suspensions with HCl, etc. Acids of the formula I, in which R' is OH, and each of R and R" is hydrogen, are crystalline white solids with high decomposition points. They can be titrated with 0.1 normal tetramethylammonium hydroxide solution in water as dibasic acids with 2 potential jumps. Thus, for example, the pK values of the acid in which R''' is methyl are 3.13 and 8.32. It may be assumed that all these acids are in the form of betaines, an assumption to which the pronounced pH dependence of the $^{31}$P chemical displacement also points. If is highly probable that the phosphinic acid proton R", and not the carboxylic acid proton R', participates in the betaine formation.

The N-substituted glycines of the formula II used as starting materials, the phosphonous acids of the formula III and the dichlorophosphines of the formula R'''-PCl$_2$, hydrolysis of which yields these acids are known ["Organic Phosphorus Compounds", ed. G. M. Kosolapoff and L. Maier, John Wiley & Sons, New York, 1972, Vol. 4, Chapters 8 and 10].

The following Examples describe the production of glycylmethylphosphinic acid derivatives of the formula I.

EXAMPLE 1

104.8 g (0.8 mole) of ethyl dichlorophosphine ($C_2H_5PCl_2$) are slowly added dropwise to 240 ml of water. Then 161.4 g (0.8 mole) of N-benzylglycine hydrochloride ($C_6H_5$—$CH_2$—NH—$CH_2$—COOH.HCl) and 240 ml of concentrated hydrochloric acid are added and the mixture is heated to reflux. Then 127.2 ml (1.6 moles) of 35% formaldehyde solution are added dropwise over 4 hours. Stirring is continued for 14 hours at 20° C. and the reaction mixture is concentrated to dryness by rotary evaporation, affording a slightly yellow, solid residue which is suspended in 1500 ml of acetone. The suspension is filtered and 172.4 g of a white crystalline solid with a melting point of 174°–176° C. (with decomp.) are obtained as residue. Concentration of the filtrate yields a further 32.3 g of product with a melting point of 178°–181° C. Total yield: 83.1%.

The resulting product is (N-benzylglycylmethyl)ethylphosphinic acid hydrochloride of the formula

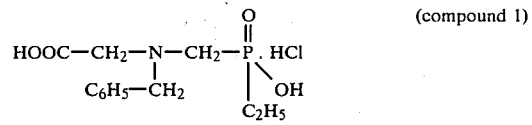

(compound 1)

Analysis: $C_{12}H_{18}NO_4P.HCl$ (307.7) calculated: C 46.84; H 6.23; N 4.55; Cl 11.52; P 10.07%. found: C 46.9; H 6.1; N 4.9; Cl 11.7; P 10.1%. $^{31}$P (in $D_2O$)= −38.7 ppm.

The acid can be titrated with tetramethylammonium hydroxide as tribasic acid.

EXAMPLE 2

The procedure of Example 1 is repeated using 58.5 g (0.5 mole) of methyl dichlorophosphine ($CH_3PCl_2$), 150 ml of water, 100.9 g (0.5 mole) of N-benzylglycine hydrochloride, 79.5 ml of 35% formaldehyde solution and 150 ml of conc. hydrochloric acid. The clear solution is concentrated by rotary evaporation, yielding 146 g (100%) of (N-benzylglycylmethyl)methylphosphinic acid hydrochloride of the formula

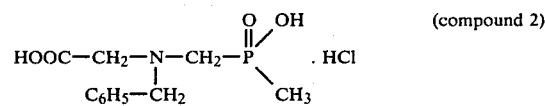

(compound 2)

as a hygroscopic solid white substance in pure form. Melting point: 60°–65° C.

Analysis: $C_{11}H_{16}NO_4P.HCl$ (293.68) calculated: C, 44.99; H 5.83; N 4.77; Cl 12.07; P 10.55%. found: C 42.3; H 6.2; N 4.9; Cl 12.0; P 10.2%. $^{31}$P(in $D_2O$)= −34.4 ppm.

EXAMPLE 3

The procedure of Example 1 is carried out starting from 9.6 g (0.1 mole) of hydroxymethylphosphonous acid

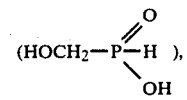

20.2 g (0.1 mole) of N-benzylglycine hydrochloride, 100 ml of conc. hydrochloric acid and 31.6 g of 38% formaldehyde solution. The reaction mixture is concentrated by rotary evaporation, yielding 22.7 g (88%) of (N-benzylglycylmethyl)hydroxymethylphosphinic acid of the formula

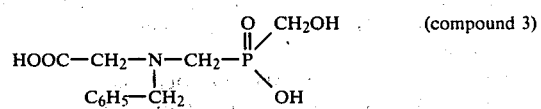

(compound 3)

as a glassy substance which sinters at 92° C., becomes liquid at 118° C., and decomposes at 135° C.

EXAMPLE 4

The procedure of Example 1 is repeated starting from 16.5 g (0.09 mole) of trichloromethylphosphonous acid $$(Cl_3C-\overset{H}{\underset{\underset{OH}{\|}}{P}})$$

in 20 ml of water, 18.5 g (0.09 mole) of $C_6H_5CH_2$—NH—$CH_2COOH \cdot HCl$, 14.3 ml of 35% formaldehyde solution and 10 ml of conc. hydrochloric acid. After standing for 12 hours at room temperature, the reaction mixture is suspended in water and the suspension is filtered, affording 23 g (71%) of (N-benzylglycylmethyl) trichloromethylphosphinic acid of the formula $$\underset{\underset{C_6H_5CH_2}{|}}{HOOC-CH_2-N-CH_2-}\overset{O}{\underset{OH}{\overset{\|}{P}}}-CCl_3 \quad \text{(compound 4)}$$

as a white crystalline powder with a melting point of 194°–195° C. (with decomp.).

Analysis: $C_{11}H_{13}Cl_3NO_4P$ (360.5) calculated: C 36.64; H 3.63; N 3.88; Cl 29.5; P 8.59% found: C 37.04; H 3.77; N 4.02; Cl 27.47; P 8.56%.

EXAMPLE 5

The procedure of Example 1 is repeated starting from 29 g (0.2 mole) of n-propyldichlorophosphine ($C_3H_7PCl_2$), 60 ml of water, 40.3 g of $C_6H_5CH_2$—NH—$CH_2CO_2H$, 34.3 g of 35% $CH_2O$ solution and 60 ml of conc. hydrochloric acid.

The reaction mixture is concentrated by rotary evaporation, affording 53.3 g of (N-benzylglycylmethyl)-propylphosphinic acid of the formula $$\underset{\underset{C_6H_5-CH_2}{|}}{HOOCCH_2-N-CH_2-}\overset{O}{\underset{OH}{\overset{\|}{P}}}\overset{CH_2CH_2CH_3}{\diagdown} \cdot (HCl) \quad \text{(compound 5)}$$

as a white crystalline substance which, after recrystallisation from water, melts at 155°–157° C. (with decomp.).

EXAMPLE 6

The procedure of Example 1 is repeated starting from 14.21 g (0.1 mole) of phenylphosphonous acid $$(C_6H_5\overset{O}{\underset{\underset{OH}{\|}}{P}}-H),$$

20.17 g (0.1 mole) of $C_6H_5CH_2$—NH—$CH_2COOH \cdot HCl$, 15.81 g of 38% formaldehyde solution (=0.2 mole of $CH_2O$), 35 ml (0.35 mole) of conc. hydrochloric acid and 25 ml of water.

The reaction mixture is left to stand at 20° C., affording 31.4 g (88%) of impure (N-benzylglycylmethyl)-phenylphosphinic acid of the formula $$\underset{\underset{C_6H_5-CH_2}{|}}{HOOC-CH_2-N-CH_2-}\overset{O}{\underset{OH}{\overset{\|}{P}}}-C_6H_5 \quad \text{(compound 6)}$$

Recrystallisation from water yields 20 g of pure crystals with a melting point of 186°–188° C.

Analysis: $C_{16}H_{18}NO_4P$ (319.3) calculated: C 60.19; H 5.68; N 4.39; P 9.70%. found: C 60.1; H 5.70; N 4.40; P 9.8%.

This acid can be titrated as dibasic acid with 2 potential jumps (first jump at pH 6.3, second jump at pH 10.2).

IR spectrum (in KBr): bands at 2.95μ (OH), 3.3μ ($C_6H_5$); 5.4μ (C=O) and 8.88μ (P=O).

EXAMPLE 7

Debenzylation is effected by dissolving 153.9 g (0.5 mole) of the compound 1 of Example 1 in 1.5 liters of glacial acetic acid, adding 15 g of 5% palladium on carbon as catalyst, and hydrogenating with $H_2$ at room temperature. The hydrogenation is complete after 1 hour and the uptake of hydrogen was 105% of the theoretical amount. The catalyst is filtered off and extracted with two 250 ml portions of hot water. The aqueous solution is concentrated and the residue is recrystallised from a mixture of water and acetone, affording 65.8 g of glycylmethylethylphosphinic acid semi-hydrochloride of the formula $$HOOC-CH_2-NH-CH_2-\overset{O}{\underset{OH}{\overset{\|}{P}}}-C_2H_5 \; 0.5 \; HCl \quad \text{(compound 7)}$$

with a melting point of 192°–194° C. (with decomp.). The mother liquor is combined with the filtrate of the hydrogenation solution and concentrated. Recrystallisation of the residue from water/acetone yields a further 15.5 g of the above compound 7 with a melting point of 189°–192° C. (with decomp.). Total yield: 81.3 g (74.7%).

Analysis: $C_5H_{12}NO_4P \cdot 0.5$ HCl (199.3) calculated: C 30.12; H 6.07; N 7.03; Cl 8.90; P 15.54%. found: C 30.2; H 6.2; N 7.1; Cl 8.90; P 15.8%. $^{31}P$ (in $D_2O$) −38.56 ppm.

Compound 7 can be titrated with $(CH_3)_4NOH$ in water with 2 potential jumps.

The monoethyl ester (esterified at the carboxylic acid group) of this dibasic acid is obtained by esterification with ethanol and hydrochloric acid. The resulting product is the hydrochloride of the ester. It has the formula $$C_2H_5-O-OC-CH_2-NH-CH_2-\overset{O}{\underset{OH}{\overset{\|}{P}}}-C_2M_5 \cdot 1 \; HCl$$

and melts at 90°–95° C. with decomposition.

EXAMPLE 8

157.3 g of the compound 2 of Example 2 are catalytically debenzylated in a mixture of 200 ml of water and 200 ml of ethanol with 7 g of 5% palladium on carbon in a manner similar to that described in Example 7. The hydrogenation was complete after 4½ hours. The catalyst is filtered off and extracted with hot water. Concentration of the aqueous extract yields a yellow oil, which crystallises from water/acetone (1:10). Yield: 51 g (57%) of white crystals with a melting point of 223°–224° C. (with decomp.) of the desired methylphosphinic acid of the formula

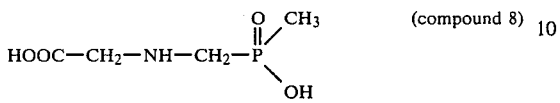
(compound 8)

Analysis: C₄H₁₆NO₄P (267.1) calculated: C 28.75; H 6.03; N 8.38; P 18.54%. found: C 28.7; H 6.3; N 8.3; P 18.3%.

The compound can also be titrated with (CH₃)₄N—OH as dibasic acid with 2 potential jumps. The isopropylamine salt of this compound melts at 203°–204° C. with decomposition.

EXAMPLE 9

64.3 g of the compound 3 of Example 3 are catalytically debenzylated in a 1:1 mixture of ethanol/water with 12 g of 5% palladium on carbon in accordance with the hydrogenation procedure described in Example 7 (reaction time 4 hours; uptake of hydrogen 102%). Evaporation of the filtrate yields 32.4 g (85%) of a viscous oil, which constitutes the hydroxymethylglycylmethylphosphinic acid of the formula

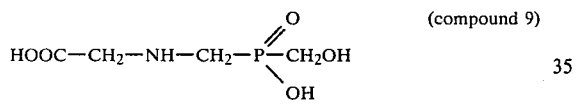
(compound 9)

The product cristallises
after standing for
several weeks and melts
at 190° C. (with decomp.).

The tert-butylamine salt of this acid melts at 130° C. with decomposition, and the cyclohexylamine salt melts at 70°–80° C.

EXAMPLE 10

21.6 g of the compound 4 of Example 4 are hydrogenated in 500 ml of glacial acetic acid with 1 g of 5% palladium on carbon as described in Example 7. When 13% of the theoretical amount of hydrogen has been taken up, a further 2 g of palladium on carbon are added until the uptake of hydrogen is 97%. The hydrogenation takes 17 hours. The catalyst is removed by filtration, the filtrate is concentrated and the yellow residue is dissolved in water. On standing, 4 g of a product which still contains benzyl groups crystallises out from the solution. The crystalline product is collected by filtration, the filtrate is concentrated and the residue (12 g) is recrystallised from water/acetone, yielding ultimately 7.43 g (45.8%) of white crystals with a melting point of 227°–229° C. (with decomp.) which constitute the trichloromethyl derivative of the formula

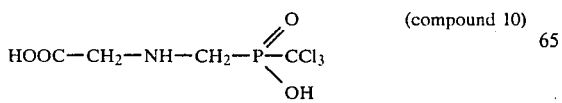
(compound 10)

Analysis: C₄H₇Cl₃NO₄P (270.4) calculated: C 17.77; H 2.61; N 5.18; Cl 39.33%. found: C 18.2; H 2.8; N 5.3; Cl 37.1%.

Compound 10 can be titrated as dibasic acid with 2 potential jumps. The monoisopropylamine salt of this compound is obtained by evaporation of an aqueous solution of equivalent amounts of the above phosphinic acid and isopropylamine.

EXAMPLE 11

53 g of the compound 5 of Example 5 are subjected to a catalytic hydrogenation with 5 g of 5% palladium on carbon in 530 ml of glacial acetic acid. When the uptake of hydrogen slows down, fresh catalyst is added. The hydrogenation is complete after 21 hours. The catalyst is removed by filtration and extracted hot twice with water. Extract and filtrate are concentrated and the residual brown oil is triturated with water/acetone, whereupon it crystallises. Yield: 27 g (70.7%) of glycylmethyl n-propylphosphinic acid of the formula

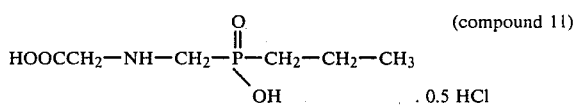
(compound 11)

which, after recrystallisation from water/acetone, melts at 196°–197° C. (with decomp.).

EXAMPLE 12

12.77 g of the compound 6 of Example 6 are hydrogenated at room temperature in 230 ml of glacial acetic with hydrogen using 1.3 g of 5% palladium on carbon as catalyst. The hydrogenation is complete after 3 hours and the theoretical amount of hydrogen was taken up. The catalyst is filtered off and the filtrate is evaporated by rotary evaporation, leaving as residue 29.4 g of greenish solid, which is dissolved hot in 180 ml of water. On cooling, 5.9 g of the phenyl derivative of the formula

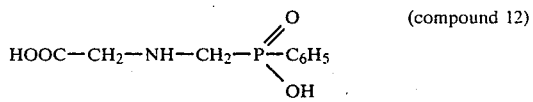
(compound 12)

crystallise out. Concentration of the filtrate to about 40 ml yields a further 1.7 g of this acid. The total yield of 7.6 g corresponds to 83% of theory. Melting point: 248°–250° C. (with decomp.).

Analysis: C₉H₁₂NO₄P (229.16) calculated: C 48.17; H 5.27; N 6.11; P 13.51%. found: C 46.95; H 5.26; N 6.09; P 13.61%.

This acid too can be titrated with (CH₃)₄N—OH as dibasic acid with 2 potential jumps.

The monoisopropylamine salt of this acid, obtained by evaporation of an aqueous solution of equivalent amounts of the acid and isopropylamine, melts at 194°–197° C. with decomposition (yield: 97%).

EXAMPLE 13

In accordance with the procedure of Example 1, 28.4 g (0.2 mole) of phenylphosphonous acid

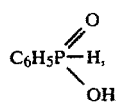

26.6 g (0.2 mole) of HN(CH$_2$COOH)$_2$, 31.6 g of 38% formaldehyde solution (0.4 mole), 20 ml of water and 30 ml (0.3 mole) of conc. hydrochloric acid are reacted for 2 hours under reflux. When the addition of formaldehyde is complete, the end product crystallises out, is collected by filtration, washed repeatedly with water and dried, affording 50.9 g (88.3%) of the compound of the formula

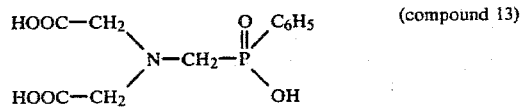

This tribasic acid forms white crystals with a melting point of 225°–230° C. (with decomp.).

Analysis: C$_{11}$H$_{14}$NO$_6$P (287.2) calculated: C 46.0; H 4.92; N 4.88% found: C 45.4; H 4.9; N 4.9%.

EXAMPLE 14

294 g of the compound 4 of Example 4 are hydrogenated in 3.5 liters of glacial acetic acid with 30 g of 5% of palladium on carbon as described in Example 7. When 15% of the theoretical amount of hydrogen has been taken up, the temperature is raised to 30° C. and a further 20 g of palladium on carbon are added. When 39% of the theoretical amount of hydrogen has been taken up, a further 100 g of palladium on carbon are added until the hydrogen uptake is 102%. The hydrogenation takes 44 hours. The catalyst is removed by filtration and the filtrate is concentrated. The residue is dissolved in 650 ml of hot glacial acetic acid. The solution is left to stand overnight, whereupon 1 g of white solid with a melting point of 230° C. crystallises out. A further 36.6 g (19.5%) of white crystals with a melting point of 231° C. (with decomp.) are obtained by concentrating the filtrate and adding acetone. These crystals constitute the dichloromethyl derivative of the formula

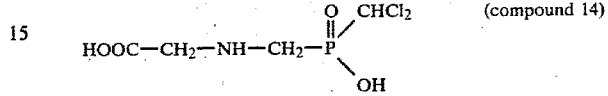

Analysis: C$_4$H$_8$Cl$_2$NO$_4$P (235.99) calculated: C 20.36; H 3.42; N 5.94; Cl 30.05%. found: C 20.35; H 3.39; N 6.12; Cl 29.84%.

The compound was further characterised by the NMR spectra:

$^1$H-NMR (in D$_2$O): PCH$_2$ at 7.73 ppm (I$_{PCH}$ $^{10}$Hz,2H); NCH$_2$C at 4.27 ppm (s,2H); PCHCl$_2$ at 6.23 ppm (I$_{pCH}$ 2 Hz, 1H); OH at 4.97 ppm(s) $^{31}$P-NMR (in D$_2$O): −18.44 ppm.

The monoisopropylamine salt is obtained in crystalline form by concentration of an aqueous solution of the acid with excess isopropylamine The following table lists further derivatives (salts and esters) of the formula I.

| Compound | Formula or designation | melting point in °C. |
|---|---|---|
| 15 | CH$_3$OOC—CH$_2$—NH—CH$_2$—P(=O)(—CH$_3$)(OH) . HCl | 110–112° |
| 16 | C$_2$H$_5$OOC—CH$_2$—NH—CH$_2$—P(=O)(—CH$_3$)(OH) . HCl | 125° |
| 17 | isopropylamine salt of compound 9 | oil |
| 18 | isopropylamine salt of compound 2 | viscous |
| 19 | C$_2$H$_5$OOC—CH$_2$—N(C$_6$H$_5$—CH$_2$)—CH$_2$—P(=O)(—CH$_3$)(OC$_2$H$_5$) | m.p. 200°/ 0.1 torr |
| 20 | C$_2$H$_5$OOC—CH$_2$—N(C$_6$H$_5$—CH$_2$)—CH$_2$—P(=O)(CH$_2$OH)(OH) | resin |
| 21 | tert-butylamine salt thereof | 78–83° |
| 22 | H$_2$N—CO—CH$_2$NH—CH$_2$—P(=O)(CH$_3$)(OH) . NH$_3$ (obtained by heating the acid with excess concentrated ammonia solution) | white solid |
| 23 | CH$_2$=CH—CH$_2$—OOC—CH$_2$—NH—CH$_2$—P(=O)(—CH$_3$)(OH) . HCl | solid, water-soluble |
| 24 | CH≡C—CH$_2$—OOC—CH$_2$—NH—CH$_2$—P(=O)(—CH$_3$)(OH) . HCl | solid, water-soluble |

| Compound | Formula or designation | melting point in °C. |
|---|---|---|
| 25 | $CH_3-OOC-CH_2-NH-CH_2-\underset{\underset{OCH_2-CH_2OH}{\mid}}{\overset{\overset{O}{\|}}{P}}-CH_3$<br>(obtained from compound 15 with ethylene oxide in dioxane at 50° C. and evaporation of the solvent) | oil |

The amides of other phosphinic acids as well as the sodium salts, the methyl, ethyl and isopropyl esters of several of these acids have also been prepared.

The novel derivatives of the formula I, both those in which R is hydrogen and those wherein R represents a substituent (benzyl etc.) possess herbicidal and plant growth-regulating properties. Both the free glycylmethylphosphinic acids and especially alkali metal and amine salts and their esters can be used in particular as contact herbicides and growth inhibitors in post-emergent application.

A number of compounds also have a fungicidal or bactericidal action.

In addition to acid addition salts, the alkali metal and alkaline earth metal salts iron salts, etc., the salts of organic amines and of protonated and quaternary nitrogen bases are to be particularly mentioned as active compounds of the present invention, in principle all cations which are tolerated by plant physiology, including those which themselves possess growth inhibiting properties.

The invention also relates to herbicidal and plant growth-regulating compositions which contain a novel derivative of the formula I as active ingredient, as well as to methods for the total and selective control of weeds in crops of cultivated plants and for inhibiting the growth of mono- and dicotyledonous plants, especially for inhibiting the growth of grasses, cereals, soya and ornamentals.

The compositions of the present invention can be in the conventional formulations as dusts, tracking powders, granulates, as dispersible concentrates, such as wettable powders, emulsions, emulsifiable concentrates and pastes, as well as solutions, especially in water.

These formulations are prepared with the conventional carriers and adjuvants by methods known in the art.

The preferred herbicidal application of the novel active compounds and compositions is post-emergent application as contact herbicide. A number of active substances are translocated in the plant and are therefore especially suitable for controlling perennial weeds.

By the use of the active compounds for inhibiting plant growth, which is also of interest, is meant a control of natural plant development which effects a slowing down of this process. By means of such a method it is possible to bring about artificially retarding phases in the plant development (sucker formation, blossoming, fruit setting etc.). The method of growth regulation is applied at a period of plant development to be determined in each individual case. The new acids of the formula I and the derivatives thereof can be applied before or after the emergence of the plants, for example to the seeds or seedlings, to roots, tubers, stems, leaves, blossoms or other parts of plants, for example by applying the active compound itself or in the form of a composition to the plants and/or by treating the nutrient medium of the plant (soil).

The primary effect attained by the novel active compounds consists in the desired reduction of the plant size, in particular of the growth in height. In general, a certain change in the form of the plant is allied to this reduction in size. As a direct consequence of the reduction of the growth in height the plant is strengthened: leaves and stems are better developed. By shortening the distances between internodes in monocotyledonous plants the breaking strength is increased. In this way it is possible to prevent to a great extent harvest losses caused by thunderstorms, prolonged rainfall etc., which usually result in a lodging of crops of cereals and leguminous plants, and thereby to facilitate harvesting. As side-effect, the reduced growth in height of useful plants result in a saving of fertilisers. This also applies equally to ornamental plants and ornamental grass plots, turf for sporting activities, or other grass-covered open spaces.

A further problem posed by pure grass cultivations, however, is the actual cutting of the grass itself, whether in open spaces of urban areas, industrial sites, playing fields, along main roads, on railway embankments or the embankments of water bodies. In all these cases it is necessary to cut the turf or grass periodically. This operation is not only time-consuming, complicated and expensive in respect of labour and machinery, but involves the personnel concerned and traffic users in considerable hazard.

For this reason there is an urgent need in areas with extensive traffic networks to maintain and tend the grassy covering for strengthening road shoulders and embankments on traffic routes on the one hand, and on the other to keep it at a reasonable height by simple means during the entire vegetation period. This need is fulfilled in a very advantageous manner by applying the novel derivatives of the formula I or a salt thereof.

The active compounds of the present invention thus intervene in the physiological processes of plant growth and are therefore growth regulators which have a growth retarding effect.

The different inhibiting effects depend substantially on the time of application, referred to the development stage of the plant, and on the concentrations employed. Accordingly, growth inhibitors can also bring about that the nutrients are beneficial to the flower and fruit formation, whereas the vegetative growth is restricted. In addition to the growth inhibition and yield increase of soya, special mention is also to be made of the suitability of many of these compounds for defoliation, for example of cotton, and as inhibitors of the suckers of tobacco plants.

The active compounds are normally applied in the form of compositions, i.e. after the addition of carriers and other ingredients.

Biological tests in support of the usefulness of the active compounds as herbicides and growth inhibitors.

Post-emergent herbicidal action (Contact herbicide)

A large number (at least 7) of weeds and cultivated plants, both mono- and dictoyledonous, were sprayed after emergence in the 4- to 6-leaf stage with an aqueous active substance emulsion in rates of 0.5, 1, 2 and 4 kg of active substance per hectare and kept at 24°–26° C. and 45–60% relative humidity. The test was evaluated 5 and 15 days after treatment in accordance with the following rating:

9=plants undamaged (as untreated control)
1=plants totally withered
8-2=intermediate stages of damage.

Of the tested compounds, the isopropylamine salt of (glycylmethyl)methylphosphinic acid, among others, exhibited a very pronounced herbicidal action against Setaria, Lolium, Solanum, Sinapis, Stellaria etc.

Growth inhibition in grasses

Seeds of the grasses Lolium perenne, Poa pratensis, Festuca ovina, and Dactylis glomerata were sown in plastic dishes filled with an earth/turf/sand mixture (6:3:1). The emergent grasses were cut back weekly to a height of 4 cm above the soil and 1 day after the last cut were sprayed with aqueous spray mixtures of an active compound of the formula I. The amount of active substance corresponded to a rate of application of 5 kg of active substance per hectare. The growth of the grasses was evaluated 10 and 21 days after application.

Growth inhibition in cereals

Spring wheat (Triticum aestivum), summer barley (Hordeum vulgare) and rye (Secale) was sown in sterilised soil in plastic beakers and reared in a greenhouse. The cereal shoots were treated 5 days after sowing with a spray mixture of the active substance. The leaf application corresponded to 6 kg of active substance per hectare. Evaluation is made 21 days later.

What is claimed is:

1. A glycylmethylphosphinic acid derivative of the formula I

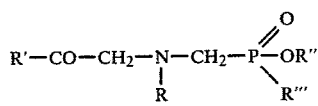

wherein
R represents hydrogen, a $C_1$–$C_6$ alkyl radical, benzyl, diphenylmethyl or triphenylmethyl, or the group HOOC—$CH_2$—,
R′ represents a —OH or —$OR_1$ group, in which $R_1$ represents a cation, a $C_1$–$C_6$ alkyl radical, a $C_1$–$C_6$ alkyl radical substituted by halogen, hydroxyl, lower alkoxy, carboxyl or cyano, a lower alkenyl or alkynyl radical, a cycloalkyl radical, or R′ represents the amino group,
R″ represents hydrogen, a cation, and lower alkyl or hydroxyalkyl,
R‴ represents a $C_1$–$C_4$ alkyl radical which can be mono- or polysubstituted by halogen atoms, hydroxyl or carboxyl groups, or represents a phenyl radical, or a phenyl radical substituted by halogen, lower alkyl, haloalkyl or di-(lower) alkylamino, and the plant physiologically acceptable salts thereof.

2. A glycylmethylphosphinic acid derivative according to claim 1, wherein R in the formula I represents hydrogen or the benzyl group.

3. A glycylmethylphosphinic acid derivative according to claim 1, wherein R in the formula I represents hydrogen and R‴ represents the methyl, trichloromethyl or hydroxymethyl group.

4. A herbicidal and plant growth-regulating composition consisting essentially of as active ingredient an effective amount of a glycylmethylphosphinic acid derivative of the formula I of claim 1, or a plant physiologically acceptable salt thereof, together with a suitable carrier therefor.

5. A method of selectively controlling weeds in postemergent application which comprises applying thereto an effective weed controlling amount of a compound of the formula I of claim 1.

6. A method of controlling the growth of mono- and dicotyledonous plants which comprises applying thereto or the locus thereof an effective plant growth controlling amount of a compound of the formula I of claim 1.

* * * * *